United States Patent [19]

Harfenist et al.

[11] Patent Number: 5,420,156
[45] Date of Patent: May 30, 1995

[54] PHARMACOLOGICALLY ACTIVE COMPOUND AND USE

[75] Inventors: Morton Harfenist, Chapel Hill, N.C.; Daniel P. C. McGee, Boulder, Colo.; Helen L. White, Chapel Hill; Barrett R. Cooper, Durham, both of N.C.

[73] Assignee: Burroughs Wellcome Co., Research Triangle Park, N.C.

[21] Appl. No.: 164,043

[22] Filed: Dec. 8, 1993

Related U.S. Application Data

[63] Continuation of Ser. No. 900,645, Jun. 18, 1992, abandoned, which is a continuation of Ser. No. 583,928, Sep. 17, 1990, abandoned.

[30] Foreign Application Priority Data

Sep. 18, 1989 [GB] United Kingdom ............... 8921069

[51] Int. Cl.$^6$ ............... C07D 327/08; A61K 31/39
[52] U.S. Cl. ............................... 514/434; 549/16
[58] Field of Search .......................... 549/16; 514/434

[56] References Cited

U.S. PATENT DOCUMENTS

| | | | |
|---|---|---|---|
| 2,997,422 | 8/1961 | Tedeschi et al. | 167/65 |
| 3,981,887 | 9/1976 | Gante et al. | 260/327 P |
| 4,012,517 | 3/1977 | Follenfant | 424/269 |
| 4,091,108 | 5/1978 | Batchelor et al. | 424/275 |
| 4,976,771 | 12/1990 | Anthony et al. | 71/90 |

FOREIGN PATENT DOCUMENTS

| | | |
|---|---|---|
| 0150891A1 | 8/1985 | European Pat. Off. . |
| 0320954A2 | 6/1989 | European Pat. Off. . |
| 0419157A3 | 3/1991 | European Pat. Off. . |
| 0419157A2 | 3/1991 | European Pat. Off. . |
| 1477032 | 8/1976 | United Kingdom . |

OTHER PUBLICATIONS

J. March, "Advanced Organic Chemistry", 2nd. edition, pp. 399–400, 1119–1120, McGraw-Hill Book Co., New York, (1977).
F. Carey, et al., "Advanced Organic Chemistry", 2nd. edition, pp. 199–202, (1983).
Abstract No. 89–179824/25, Nippon Oils & Fats KK, N10F, Dec. 15, 1987.
Harfenist, et al., J. Med. Chem. vol. 34, No. 9, pp. 2931–2933, (Sep. 1991).

*Primary Examiner*—Richard L. Raymond
*Attorney, Agent, or Firm*—Donald Brown; Lawrence A. Nielsen

[57] ABSTRACT

1-Ethylphenoxathiin 10,10-dioxide (I)

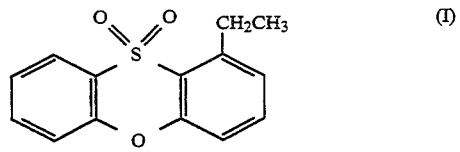

inhibits monoamine oxidase-A and is useful in the treatment of disorders such as depression.

11 Claims, No Drawings

PHARMACOLOGICALLY ACTIVE COMPOUND AND USE

PRIOR APPLICATION

This application is a continuation of U.S. patent application Ser. No. 07/900,645 filed Jun. 18, 1992, now abandoned, which is a division Ser. No. 07/583,928 filed Sep. 17, 1990, now abandoned.

Monoamine oxidase (MAO) is the enzyme in brain principally responsible for intraneuronal oxidation of biogenic amine neurotransmitters to inactive forms. It is understood to occur as two independent forms, normally designated MAO-A and MAO-B (White and Glassman, *J. Neurochem.*, 29, 989–997, (1977) and Tipton et al., "Monoamine Oxidase and its Selective inhibitors", Beckmann and Riederer, Eds. *Mod. Probl. Pharmacopsychiat.*, 19 15–30, Karger, Basel (1983)). MAO inhibition has been found to elevate neurotransmitter concentrations in the brain.

MAO inhibitors are used therapeutically in the treatment of a wide variety of conditions, especially depression, particularly when characterized by anxiety, obsessional neuroses, or appetite disorders. However, a number of such compounds, for example isocarboxazid, pheneizine and tranylcypromine, are non-selective, irreversible inhibitors of the enzyme and are characterised by an undesirable side effect associated with ingestion of food or drink containing a high level of tyramine, for example, certain cheeses. When a patient receiving such a drug ingests such a product, then his blood pressure may be raised, sometimes to a dangerous level. Such patients are therefore instructed to avoid foods and beverages of this nature.

Patent publication EP-A-0 150 891 discloses the thioxanthen-9-ones represented by the formula

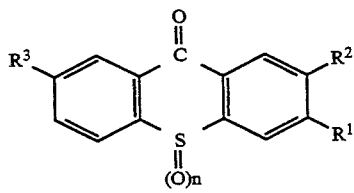

wherein n is 0, 1 or 2, and physiologically acceptable salts thereof, and teaches them to be inhibitors of MAO-A and useful in the prophylaxis and treatment of mental disorders such as depression.

The present invention provides the novel compound 1-ethylphenoxathin 10,10-dioxide, (I), hereinafter also referred to as "Compound I"

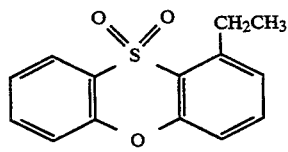

which is distinct from isocarboxazid and the like in being a selective, reversible inhibitor in mammals of MAO-A. Compound is it also useful as an antidepressant.

Compound I is reversibly bound to MAO-A as shown by its removal from its complex with MAO-A by dialysis.

No pharmacologically significant increase in response (elevation of blood pressure) has been observed in test mammals which have been given oral antidepressant doses of Compound I prior to orally ingested tyramine.

The present invention further includes a method of inhibiting monoamine oxidase-A (MAO-A) in the brain of mammals including human beings. This method comprises the administration to a mammal, which has been identified as being in need of inhibition of brain monoamine oxidase-A, of 1-ethylphenoxathiin, 10,10-dioxide in an amount sufficient to inhibit the MAO-A in the brain.

This invention also includes a method of treatment of depression in a human being identified as having depression. This method comprises the administration of a therapeutically effective depression treatment amount of 1-ethylphenoxathiin 10,10-dioxide to a human being identified as having depression.

Depression states in which this compound is particularly useful are those defined in the *Diagnostic and Statistical Manual of Mental Disorders*, third edition (DSM III), American Psychiatric Association, Washington, D.C. (1980), (DSM III, 296,2X to 296.6X and 301.13), including that characterized by anxiety or obsessional neuroses (DSM III, 300.40), or atypical depression (DSM III, 296.70 and 296.82), e.g., accompanied by a personality disorder. Other therapeutic uses for Compound I include treatment of post-traumatic stress disorder (DSM III, 308,30 and 309,81), obsessive compulsive behavioral states (DSM III, 300.30), anxiety states (DSM III, 300.00, 300.01, 300.02, 300.21, 300.22, 300.23 and 300.29), e.g., which are accompanied in an acute phase by panic attacks with or without phobia (DSM III 300.21), phobia (DSM III 300.23 and 300.29), appetite disorders, e.g., bulimia (DSM III, 307.51) and anorexia (DSM III, 307.10), and borderline personality disorder (DSM III, 301.83) in human beings identified as having such disorders. Still further therapeutic uses for Compound I include treatment of headaches, e.g., migraine, muscle contraction and mixed (i.e., combination of migraine and muscle contraction) headaches in human beings having such headaches.

Compound I may be administered by, for example, the oral, rectal or parenteral route. In general, the compound may be administered for the treatment of each of the disorders stated hereinabove, including depression, in the dosage range of about 0.1 mg to about 50 mg per kg of human body weight per day, preferably about 1 mg to about 40 mg per kg of human bodyweight per day and optimally about 10 mg per kg of human bodyweight per day, although the precise dosage will naturally depend on a number of clinical factors, for example, the age of the recipient, the route of administration and the condition under treatment and its severity: for administration of Compound I by the oral route, a dosage regime of 0.3 to 30 mg per kg per day, preferably 2 to 20 mg per kg per day and optimally about 10 mg per kg per day, may be used. The desired daily dose is preferably given as two or three or more subdoses administered at appropriate intervals during the day. These subdoses may be presented in unit dosage form each containing, for example, from 100 to 500 mg, preferably 200 mg, of Compound I.

While it is possible to administer Compound I as the raw chemical, it is highly desirable to administer it in the form of a pharmaceutical formulation.

The present invention thus further provides pharmaceutical formulations comprising 1-ethylphenoxathiin 10,10-dioxide together with an acceptable carrier therefor; the carrier should be acceptable in the sense of being compatible with the other ingredients and not deleterious to the recipient thereof. The formulations may be adapted for oral, parenteral or rectal administration.

The formulations may conveniently be presented in unit dosage form and may be prepared by any of the methods well known in the art of pharmacy. Such methods include the step of bringing into association the active ingredient with the carrier which may comprise one or more accessory ingredients. In general the formulations are prepared by uniformly and intimately brining into association the active ingredient with liquid carriers or finely divided solid carriers or both, and then, if necessary, shaping or encapsulating the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion.

A tablet may be made by compression or molding, optionally with one or more accessory ingredients. Compressed tablets may be prepared by compressing in a suitable machine the active ingredient in a free-flowing form such as a powder of granules, optionally mixed with a binder, lubricant, inert diluent, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for rectal administration may be presented as a suppository with the usual carriers such as cocoa butter.

Formulations suitable for parenteral administration include aqueous sterile injection solutions which may contain antioxidants, buffers, bacteriostats and solutes which renders the formulation isotonic with the blood of the intended recipient; and aqueous and nonaqueous sterile suspensions which may include suspending agents and thickening agents. The formulations may be presented in unit dose or multidose containers, for example sealed ampoules and vials, and may be stored in a freeze dried (lyophilized) condition requiring only the addition of the sterile liquid carrier, for example PEG 400: ethanol mixtures, immediately prior to use. Extemporaneous injection solutions and suspensions may be prepared from sterile powders,granules and tablets of the kind previously described.

Preferred unit dosage formulations are those containing a daily dose or unit daily subdose, as hereinabove recited, or an appropriate fraction thereof, of the active ingredient.

It should be understood that in addition to the ingredients particularly mentioned above the formulations of this invention may include other agents conventional in the art having regard to the type of formulation in question, for example, those suitable for oral administration may include flavouring agents.

Compound I may be prepared by those methods known in the art for the synthesis of compounds of analogous structure and in this regard reference is made, by way of illustration only, to the following standard texts:

i) "Protective Groups in organic Chemistry" ed. J. F. W. McOmie, Plenum Press (1973), ISBN 0-306-30717-0.

ii) "Compendium of Organic Synthetic methods" ed. I. T. Harrison and S. Harrison, Wiley-Interscience, Vol. I (1971) ISBN 0-471-35550-X, Vol. II (1974) ISBN 0-471-35551-8 and Vol. III (ed. L. S. Hegedus and L. Wade) (1977) ISBN 0-471-36752-4.

iii) Rodd's "Chemistry of Carbon Compounds" second edition, Elsevier Publishing Company.

All references identified hereinabove or in the following are hereby incorporated herein by reference thereto.

1. One method comprises selective oxidation of a 1-ethylphenoxathin (II)

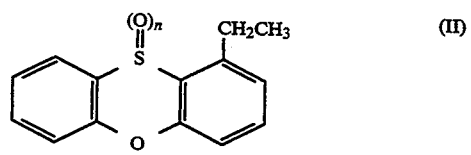

wherein n is 0, or 1, using for example hydrogen peroxide or a percarboxylic acid (such as peracetic acid or perbenzoic acid) in a solvent such as acetic acid or acetone, preferably at a temperature above room temperature, chromatic anhydride or potassium permanganate.

The compound ((II); n is 1) may be prepared by selective partial oxidation of ((II); n is 0) using for example sodium metaperiodate, iodosobenzene diacetate or, at or somewhat below room temperature, a limited amount of hydrogen peroxide or of a percarboxylic acid (vide supra).

The compound ((II); n is 0) may in turn be prepared by reaction of 2-mercaptophenol (III) with a nitrogenzene (IV)

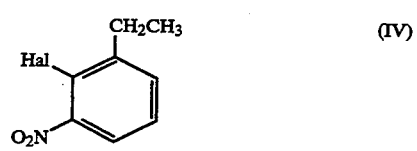

wherein Hal is halo, for example, chloro, bromo or iodo; the reaction is preferably effected in the presence of an excess (i.e. slightly more than one equivalent) of a strong base (for example, potassium carbonate, potassium t-butoxide or sodium hydroxide) in a protic solvent such as ethanol or a polar, aproptic solvent such as N,N-dimethylformamide, or in an aqueous/water-immiscible organic solvent combination (preferably) in the presence of a phase transfer catalyst.

2. A further method comprises reaction with an ethyl halide (for example, the chloride, bromide or iodide) of a phenoxathiin 10,10-dioxide (V)

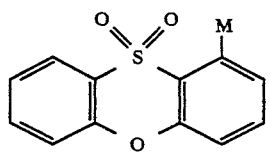

wherein M is an alkali metal, for example, lithium, sodium or potassium; the reaction may conveniently be effected in an aprotic solvent such as an ether (for example, tetrahydrofuran) or hydrocarbon, at a temperature of from about −50° C. to about room temperature.

The compound (V) may be prepared by reacting phenoxathiin 10,10-dioxide with an appropriate organometallic compound, for example, n-butyllithium, in an approptic solvent such as an ether (for example, tetrahydrofuran) or hydrocarbon, preferably at a temperature of from about −40° C. to about −80° C.; when prepared in this manner the compound (V) may conveniently be reacted in situ with an ethyl halide, as above described, to provide Compound I.

Phenoxathiin 10,10-dioxide may be prepared by oxidation of phenoxathiin using hydrogen peroxide or a percarboxylic acid (such as peracetic acid or perbenzoic acid) in a solvent such as acetic acid or acetone, preferably at a temperature above room temperature. Alternatively, chromic anhydride or potassium permanganate may be employed as the oxidising agent.

Phenoxathiin is commercially available from Parish Chemical Co. (145 N. Geneva Rd., Orem, Utah 84057, U.S.A.) or may be made by the method of *Organic Synthesis*, Coll. Vol. II, page 485.

3. A yet further method comprises selective reduction of a phenoxathiin 10,10-dioxide (VI)

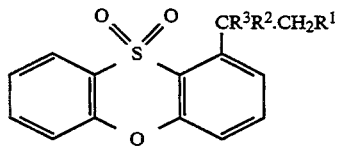

wherein $R^1$ is hydrogen and either $R^2$ is hydrogen and $R^3$ is halo or hydroxyl or $R^2$, $R^3$ and the carbon atom to which they are attached together form a carbonyl group, or $R^3$ is hydrogen and $R^1$ and $R^2$ together form a bond.

The halo identity for $R^3$ may be, for example, chloro, bromo or iodo.

As will be appreciated, the agents and conditions that may be employed depend upon the identities as above recited of $R^1$, $R^2$ and $R^3$ and following is provided purely by way of illustration of the available techniques.

Thus, reduction of ((VI); $R^1$, $R^2$ are hydrogen, $R^3$ is halo) may be effected using sodium or zinc/copper with ethanol, lithium aluminium hydride or tin with hydrochloric acid, whilst for ((VI); $R^3$ is hydrogen, $R^1$, $R^2$ together form a bond) hydrogenation using a platinum, palladium or nickel catalyst is appropriate.

For the compounds ((VI); $R^1$, $R^2$ are hydrogen, $R^3$ is hydroxyl) and ((VI); $R^1$ is hydrogen, $R^2$, $R^3$ and the carbon atom to which they are attached together form a carbonyl group) suitable reagents include concentrated hydriodic acid with red phosphorus and either sodium borohydride pellets or triethylsilane with trifluoroacetic acid; hydrogenation using a noble metal catalyst such as Pearlman's catalyst (20% palladium hydroxide on carbon) may also be employed. Reduction of the carbonyl compound may also be carried out using amalgamated zinc with concentrated hydrochloric acid (Cemmensen reaction) or hydrazine hydrate and potassium hydroxide with a suitable high-boiling solvent such as ethylene glycol (Huang Minion modification of the Wolff-Kishner reaction).

The compounds (VI) may be prepared either directly or indirectly from a compound (V). Thus, reaction of the latter with an acetyl halide or alkyl (C1-C5) acetate affords the carbonyl compound (VI) whilst with acetaldehyde there results ((VI); $R^1$, $R^2$ are hydrogen, $R^3$ is hydroxyl). This last may in turn be converted to ((VI); $R^1$, $R^2$ are hydrogen, $R^3$ is halo) using for example a phosphorus halide, thionyl chloride with pyridine or triphenylphosphine and carbon tetrabromide with diethylazodicarboxylate, and to ((VI); $R^3$ is hydrogen, $R^1$, $R^2$ together form a bond) by dehydration with for example p-toluenesulphonic acid and a suitable solvent (with azeotropic removal of the resulting water) or boiling dilute sulphuric acid.

The following Examples illustrate the present invention.

EXAMPLE 1

1-Ethylphenoxathiin 10,10-dioxide

A. Phenoxathiin 10,10-dioxide

To a slurry of phenoxathiin (81 g. Parish Chemical Co., Orem, Utah) in glacial acetic acid (250 mL) was added 30% hydrogen peroxide (250 mL). The mixture was heated with stirring at reflux for 2.5 hr and then allowed to cool overnight. It was heated at reflux for an additional 2 hr and cooled to room temperature. The white solid produced was collected by filtration and thoroughly washed with water (until acid-free and peroxide-negative), then dried in vacuo at 55° C. to give phenoxathiin 10,10-dioxide (87 g), mp 145°–146° C.

B. 1-Ethylphenoxathiin 10,10-dioxide

A mixture of phenoxathiin 10,10-dioxide (50.5 g) in dry tetrahydrofuran (500 mL) under nitrogen was cooled in an acetone/dry ice bath. To this slurry was added a 1.6 M solution of n-butyllithium in hexane (144 mL) at a rate which maintained the reaction temperature at −40° C., resulting after 30–45 min. in an orange solution of 1-lithiophenoxathiin 10,10-dioxide. To this solution was added ethyl iodide (35 mL), after which the reaction mixture was allowed to warm to room temperature. After about 3–4 hr the yellow solution was partially evaporated under reduced pressure and was then partitioned between methylene chloride and water. The methylene chloride phase was washed with dilute hydrochloric acid, dried over anhydrous magnesium sulfate and evaporated to a yellow residue which was purified by column chromatography on Silica Gel 60 (E. Merck, Darmstadt, Germany) eluting with toluene. The desired fractions were combined and evaporated, and the residue was crystallized from ethyl acetate/pentane to give 1-ethylphenoxathiin 10,10-dioxide, mp. 112°–114° C. (del. 102°–104° C.).

EXAMPLE 2

1-Ethylphenoxathiin 10,10-dioxide

A. 1-(1-Hydroxyethyl)phenoxathiin 10,10-dioxide

To a batch of 1-lithiophenoxathiin 10,10-dioxide, prepared according to the procedure of Example 1B from 44 g of phenoxathiin 10,10-dioxide chilled to $\leq -50°$ C. in a dry ice/acetone bath, was slowly added chilled acetaldehyde (20.37 g). The reaction mixture was maintained at $-50°$ C. during the addition which took 45 min. It was then allowed to warm to room temperature, and the solvent was removed under reduced pressure. The yellow-orange residue was stirred overnight with 0.5 N hydrochloric acid (259 mL), filtered and washed with water (500 mL). It was then washed throughly with ethanol (1.5 L), filtered and dried to give 1-(1-hydroxyethyl) phenoxathiin 10,10-dioxide (41 g) which was sufficiently pure for the next step (conversion to 1-ethylphenoxathiin 10,10-dioxide).

A sample was recrystallized from ethyl acetate/hexanes to given an analytically pure sample of 1-(1-hydroxyethyl)phenoxathiin 10,10-dioxide as white crystals, mp. 177°–179° C.

Anal. Calcd.: $C_{14}H_{12}O_4S$: C, 60.83; H, 4.38; S, 11.60. Found: C, 60.78; H, 4.40; S, 11.51.

$^1$H-NMR (DMSO-$d_6$) $\delta$8.06 (dd, 1H, H9, J=7.9, 1.3), 7.83 (m, 1H, H7 or H8), 7.79 (d, 1H, H2 or H4, J=7.6), 7.77 (m, 1H, H7 or H8), 7.57 (d, 1H, H2 or H4, J=7.7), 7.53 (m, 1H, H2), 7.46 (dd, 1H, H6, J=7.6, 2.0), 5.74 (m, 1H, —C$\underline{H}$(OH)—CH$_3$), 5.65 (d, 1H, —OH, J=4.2), 1.45 (d, 3H, methyl, J=5.8).

B. 1-Ethylphenoxathiin 10,10-dioxide

A solution of 1-(1-hydroxyethyl)phenoxathiin 10,10-dioxide (590.2) g) in acetic acid (5.4 L) containing 70% aqueous perchloric acid (250 mL) was blanketed with nitrogen and 65 g of Pearlman's catalyst (20% palladium hydroxide on carbon, Aldrich Chemical Co., Milwaukee, Wis.) was added. The atmosphere above the reaction mixture was replaced by successive evacuation and flushing with nitrogen, and then the nitrogen was displaced by successive evacuations and flushings with hydrogen. The reaction mixture was then stirred vigorously and hydrogen was added until no more was taken up. The catalyst was filtered off and rinsed with acetic acid. The combined acetic acid solutions were diluted to approximately 23.5 L with water and stirred overnight at room temperature. The resulting off-white solid was collected by filtration, washed with water (2 L) and dried at 50° C. in a vacuum oven, giving 1-ethylphenoxathiin 10,10-dioxide. After recrystallization from ethyl acetate/hexanes it had a melting point of 114°–115° C. Recrystallization from ethyl acetate/pentane appeared to give a different crystalline form, mp 101°–103° C.

Anal. Calcd: $C_{14}H_{12}O_3S$: C, 64.60; H, 4.65; S, 12.32. Found: C, 64.49; H, 4.69; S, 12.27.

$^1$H-NMR (DMSO-$d_6$) $\delta$8.05 (dd, 1H, H9, J=7.9, 1.5), 7.80 (ddd, 1H, H7, J=8.4, 7.5, 1.5), 7.70 (dd, 1H, H3, J=8.1, 8.1), 7.53 (d, 1H, H6, J=8.5), 7.52 (dd, 1H, H8, J=7.7, 7.7), 7.38 (d, 1H, H4, J=8.6), 7.35 (d, 1H, H2, J=7.9), 3.17 (q, 2H, methylene, J=7.2), 1.32 (t, 3H, methyl, J=7.3).

EXAMPLE 3

Pharmaceutical Formulations

In the following formulation examples, 'Active ingredient' means 1-ethylphenoxathiin 10,10-dioxide, i.e. Compound I.

A. 100 mg Compression Coated Tablet

|  | Ingredients | Amount Per Tablet |
|---|---|---|
| Core | Active Ingredient | 100 mg |
|  | Cornstarch | 25 mg |
|  | Magnesium Stearate | 2 mg |
| Coating | Coating Lactose | 320 mg |
|  | Cornstarch | 50 mg |
|  | Gelatin | 6 mg |
|  | Magnesium Stearate | 4 mg |

The Active ingredient and starch are granulated with water and dried. Magnesium stearate is added to the dried granules. Lactose and starch are granulated with a 10% w/v aqueous solution of gelatin and dried. Magnesium stearate is added to the dried granules. The granulated ore is compressed with the granulated coating in a conventional compression molding machine.

B. 200 mg Capsule

| Ingredients | Amount Per Capsule |
|---|---|
| Active Ingredient | 200 mg |
| Lactose | 200 mg |
| Talc | 40 mg |

The Active ingredient, lactose and talc are brought into intimate admixture with one another and 440 mg of the resultant mixture is introduced into a size 0 hard gelatin capsule.

C. 100 mg Capsule

| Ingredients | Amount Per Capsule |
|---|---|
| Active Ingredient | 100 mg |
| Lactose | 100 mg |
| Cornstarch | 100 mg |
| Magnesium Stearate | 10 mg |

The ingredients are mixed together until homogeneous and 310 mg of the resulting mixture filled into each hard gelatin capsule.

D. 100 mg Capsule

| Ingredients | Amount Per Capsule |
|---|---|
| Active Ingredient | 100 mg |
| Gelucire 37/02 | 400 mg |
| PEG 3350 | 50 mg |

The Gelucire 37/02 is melted by heating at 90° C. the PEG 3350 is added, and the mixture is stirred to give a uniform melt. While monitoring the temperature at 90° C., the Active Ingredient is added and the mixture stirred to give a homogeneous mixture. The mixture is added to size 0 hard gelatin capsules, cooled and capped. Gelucire 37/02 is a trademark of Gattefosse Corporation of Elsmford, N.Y. for hydrogenated polyglycolized glycerides prepared from C10-18 hydrogenated fatty acids, glycerol and PEG 300. PEG 300 is poly(ethylene glycol) of approximate molecular weight 300; PEG 3350 is poly(ethylene glycol) of approximate molecular weight 3350.

E. 100 mg Capsule

| Ingredients | Amount Per Capsule |
| --- | --- |
| Active Ingredient | 100 mg |
| Labrafil M 1944 CS | 400 mg |

The Labrafil is heated to about 70° C., and the Active ingredient is then added with stirring to give a homogeneous mixture. The mixture is added to size 0 hard gelatin capsules, cooled and capped. Labrafil M 1944 CS is a trademark of Gattefoose Corporation of Elmsford, N.Y. for unsaturated polyglycolized glycerides, prepared from apricot kernel oil and PEG 300.

F. 500 mg Tablet

| Ingredients | Amount Per Tablet |
| --- | --- |
| Active Ingredient | 500 mg |
| Cornstarch | 100 mg |
| Microcrystalline Cellulose | 75 mg |
| Magnesium Stearate | 5 mg |
| Granulated polyvinylpyrrolidone (10% w/v in 50% w/v aqueous ethanol) | 10 mg |

The Active Ingredient, corn starch and microcrystalline cellulose are mixed together, and granulated with the alcoholic polyvinylpyrrolidone. The resulting granules are dried, and compressed to produce tablets, each tablet having a weight of approximately 690 mg.

G. Suppository

| Ingredients | Amount Per Suppository |
| --- | --- |
| Active Ingredient | 200 mg |
| Suppository Base | q.s. to 2 g |

The Active Ingredient in fine powder form is dispersed into a little of the molten Suppository Base at 50° C. The dispersion is incorporated into the bulk of the base at the same temperature, allowed to cool at 42°–45° C., poured into suitable 2 g suppository molds and allowed to set at 15°–20° C. Suitable suppository bases are Massa Esterinum C (Henkel International, Dusseldorf, Germany) and Witten H Suppository Compound.

H. Dispersible Tablet

| Ingredients | Amount Per Tablet |
| --- | --- |
| Active Ingredient | 200 mg |
| Corn Starch | 40 mg |
| Primojel (Trade name: sodium starch glycollate (125#m powder)) | 50 mg |
| Dicalcium Phosphate Dehydrate | 50 mg |
| Sodium Carboxymethyl Cellulose | 2 mg |
| Sodium Saccharin | 5 mg |
| Microcrystalline Cellulose | 50 mg |
| Magnesium Stearate | 3 mg |

The Active Ingredient, half of the corn starch, the Primojel and dicalcium phosphate dihydrate are mixed together and then granulated with a solution of sodium carboxymethyl cellulose and sodium saccharin in a suitable volume of 50% ethyl alcohol. The granules are dried, the remaining corn starch, the microcrystalline cellulose and the magnesium stearate are blended-in and the resulting mixture compressed into tablets.

EXAMPLE 4

Biological Activity

I. MONOAMINE OXIDASE INHIBITION

A. In Vitro inhibition

MAO was assayed with [$^3$H]serotonin (0.2 mM, 5G/mole) and [$^{14}$C]β-phenethylamine (10 μM, 3 G/mole) as substrate in a double-label assay (White and Glassman, J. Neurochem, 29:987–97 (1977)). Under these conditions, serotonin is selectively metabolised by MAO-A and β-phenethylamine by MAO-B.

For studies of the kinetic mechanism of inhibition, the above method was used except that a single substrate, serotonin or tyramine, was varied over a 10-fold concentration range that included the $K_m$ concentration. When tyramine was used as substrate, the extract was pretreated with deprenyl (1 μM) to inhibit all MAO-B activity. MAO-A activity was determined in the absence and presence of the compound under test at each substrate concentration in duplicate or triplicate assays.

Compound I produced a potent selective inhibition of MAO-A in mitochondrial extracts of rat or human brain, the $I_{50}$ (concentration producing 50% inhibition) being 0.035 μM. This inhibition was competitive vs. the substrate serotonin or tyramine, the $K_i$ being 0.01 μM with either.

B. In Vivo inhibition

To determine MAO inhibition in brains and livers of rats pretreated with a reversible inhibitor, it was necessary to use an assay procedure that minimized dilution of the compound. Thus, high concentrations of tissue homogenates were incubated for very short periods of time. For brain assays, initial tissue was 3-fold diluted into each assay. Because of the very high MAO activity. Further dilution of liver homogenates was necessary in order to obtain reliable data. Substrate concentrations were not saturating, but were chosen relative to $K_m$ values for serotonin and β-phenethylamine in order to give an estimate of MAO-A and MAO-B, respectively. Brains from pretreated male Sprague-Dawley rats (sacrificed 3 hours after oral dosing with the test compound) were homogenized in a buffer consisting of 0.1 M potassium phosphate and 5% sucrose (pH 7.4) at a 1:1 tissue weight/buffer volume ratio, using a motorized Teflon/glass homogenizer. MAO-A and MAO-B were determined by incubating 100 μL of tissue homogenate with 50 μL of a double-label substrate mixture to give final concentrations of [$^3$H]serotonin, 0.4 mM (5C/mole) and [$^{14}$C]β-phenethylamine, 20 μM (3C/mole). For blank assays, 100 μL portions of homogeneous were pre-incubated for 15 min. at 37° C. with pargyline (4 mM) before substrate addition. Incubations with substrate present were at 37° C. for 30 sec. Assay mixtures were then acidified and products extracted as in the above in vitro method (White and Glassman, loc. cit.).

Liver tissue was homogenized in the above phosphate-sucrose buffer at a 1:5 tissue weight/buffer volume ratio. Portions (100 μL) of homogenate were incubated with 50 μL of the above double-label substrate mixture. Blank assays included the same volume of homogenate pre-incubated with 4 mM pargyline for 15 min. at 37° C. After addition of substrates, mixtures were incubated at 37° C. for 30 sec, acidified, and products extracted as above.

For Compound I, the following results were obtained.

| Dose | Percentage inhibition of MAO-A | |
|---|---|---|
| (mg/kg p.o.) | Brain | Liver |
| 5 | 18.5 ± 8.1 | 32.8 ± 6.4 |
| 10 | 65.2 ± 6.6 | 61.8 ± 4.4 |
| 20 | 82.4 ± 2.6 | 78.9 ± 1.6 |

There was no significant inhibition of MAO-8 in either tissue.

In other experiments with compound I, for an oral dose of 20 mg/kg, inhibition of brain MAO-A was found to peak within 1-6 hours and to be negligible at 24 hours after dosing, indicating reversibility of the in vivo inhibition.

II. EFFECTS ON BLOOD PRESSURE RESPONSE TO ORAL TYRAMINE

Compound I was tested for effects on the pressor response induced by orally administered tyramine in a conscious, unrestrained rat model. The method involves direct measurement of mean arterial blood pressure from a cannula implanted in a carotid artery and exteriorized through a small incision in the back of the neck. Peak changes in the pressor response following tyramine (p.o.) in animals pretreated with Compound I (p.o.) were compared with changes seen in animals pretreated with either the known MAO inhibitor, pheneizine, (p.o.) or vehicle (water) alone.

To compare effects at equipotent doses that are relevant to antidepressant activity, either Compound I or pheneizine was given in a single oral dose that produced approximately 80% inhibition of brain MAO-A by the time of tyramine administration, 3 hours later. Under these conditions, liver MAO-A was inhibited by 90% or more by pheneizine.

Rates pretreated with vehicle alone exhibited blood pressure elevations at relatively high doses of tyramine, i.e. above 27 mg/kg. Compound I (25 mg/kg, p.o.) did not cause a statistically significant increase in the pressor response to tyramine at threshold tyramine doses (15 mg/kg), while pheneizine (50 mg/kg, p.o.) caused a 57.5 (±3.6) % increase in mean arterial blood pressure in response to the same dose of tyramine.

III. TOXICITY

No visible effects occurred in mice or rats after acute doses of Compound I up to 1000 mg/kg., p.o.

We claim:
1. 1-Ethylphenoxathiin 10,10-dioxide.
2. A pharmaceutical formation comprising 1-ethylphenoxathiin 10,10-dioxide together with an acceptable carrier therefor.
3. A formulation according to claim 2 adapted for oral administration.
4. A formulation according to claim 3 in the form of a capsule or tablet.
5. A method of treating depression, an obsessive compulsive disorder or anxiety in a human in need thereof which comprises administering an effective amount of 1-ethylphenoxathiin 10,10-dioxide.
6. A method for the treatment of depression in a human being comprising the administration to said human being of an antidepressant amount of 1-ethylphenoxathiin 10,10-dioxide.
7. A method according to claim 6 wherein said 1-ethylphenoxathiin 10,10-dioxide is administered by the oral route.
8. A method according to claim 7 wherein said 1-ethylphenoxathiin 10,10-dioxide is administered together with an acceptable carrier therefor.
9. A method according to claim 8 wherein said 1-ethoxyphenoxathiin 10,10-dioxide is administered in the form of an orally ingestible capsule or tablet.
10. A method for the treatment of obsessive compulsive disorder in a human being comprising the administration to said human being of an effective obsessive compulsive disorder treatment amount of 1-ethylphenoxathiin 10,10-dioxide.
11. A method for the treatment of anxiety in a human being comprising the administration to said human being of an effective anxiety treatment amount of 1-ethylphenoxathiin 10,10-dioxide.

* * * * *